United States Patent
Song et al.

(10) Patent No.: US 10,017,472 B2
(45) Date of Patent: Jul. 10, 2018

(54) HYDRATE OF 2-ISOPROPOXY-5-METHYL-4-(PIPERIDIN-4-YL) ANILINE DIHYDROCHLORIDE, PREPARATION METHOD AND USE OF THE SAME

(71) Applicant: 2Y-CHEM, LTD., Shanghai (CN)

(72) Inventors: Jinfeng Song, Shanghai (CN); Xungui He, Shanghai (CN); Wensheng Tang, Shanghai (CN); Yuan Wang, Shanghai (CN)

(73) Assignee: 2Y-CHEM, LTD., Shanghai (CN)

( * ) Notice: Subject to any disclaimer, the term of this patent is extended or adjusted under 35 U.S.C. 154(b) by 0 days.

(21) Appl. No.: 15/561,730

(22) PCT Filed: Mar. 2, 2016

(86) PCT No.: PCT/CN2016/075354
§ 371 (c)(1),
(2) Date: Sep. 26, 2017

(87) PCT Pub. No.: WO2016/150283
PCT Pub. Date: Sep. 29, 2016

(65) Prior Publication Data
US 2018/0086706 A1 Mar. 29, 2018

(30) Foreign Application Priority Data
Mar. 26, 2015 (CN) .......................... 2015 1 0136779

(51) Int. Cl.
*C07D 213/26* (2006.01)
*C07D 401/12* (2006.01)
(Continued)

(52) U.S. Cl.
CPC .......... *C07D 211/18* (2013.01); *B01D 9/0054* (2013.01); *B01D 9/0063* (2013.01); *B01D 2009/0095* (2013.01)

(58) Field of Classification Search
CPC ... C07D 211/18; B01D 9/0054; B01D 9/0063
(Continued)

(56) References Cited

FOREIGN PATENT DOCUMENTS

| CN | 103992262 A | 8/2014 |
|---|---|---|
| CN | 104447515 A | 3/2015 |

(Continued)

OTHER PUBLICATIONS

Song; CN 104447515, Abstract and unverified machine translation, Mar. 25, 2015. (Year: 2015).*

(Continued)

*Primary Examiner* — Daniel R Carcanague
(74) *Attorney, Agent, or Firm* — Carter, DeLuca, Farrell & Schmidt, LLP

(57) ABSTRACT

The present invention relates to 2-isopropoxy-5-methyl-4-(piperidin-4-yl) aniline dihydrochloride monohydrate and a preparation method of the same. The 2-isopropoxy-5-methyl-4-(piperidin-4-yl) aniline dihydrochloride monohydrate has a very good crystal form and is well suitable for recrystallization purification; further, the effect of impurity removal effect is very good, and any single impurity can be controlled less than 0.1%.

3 Claims, 2 Drawing Sheets

(51) Int. Cl.
*C07D 211/18* (2006.01)
*B01D 9/00* (2006.01)

(58) Field of Classification Search
USPC .......................................................... 546/192
See application file for complete search history.

(56) References Cited

FOREIGN PATENT DOCUMENTS

| CN | 104803908 A | 7/2015 |
| WO | 2009126515 A1 | 10/2009 |
| WO | WO 2014173291 | * 10/2014 |
| WO | WO 2016138648 | * 9/2016 |

OTHER PUBLICATIONS

International Search Report for International Application No. PCT/CN2016/075354 dated May 30, 2016.
"Crystalline forms of 2-isopropoxy-5-methyl-4-(piperidin-4-yl)aniline dihydrochloride and 2,5-dichloro-N-(2-(isopropylsulfonyl)phenyl)pyrimidin-4-amine", An IP.com Prior Art Database Technical Disclosure, Nov. 18, 2014.

* cited by examiner

HYDRATE OF 2-ISOPROPOXY-5-METHYL-4-(PIPERIDIN-4-YL) ANILINE DIHYDROCHLORIDE, PREPARATION METHOD AND USE OF THE SAME

CROSS REFERENCE TO RELATED APPLICATIONS

This application is a national stage application of International Application No. PCT/CN2016/075354, filed Mar. 2, 2016, which claims the benefit of and priority to Chinese Patent Application No. 201510136779.4, filed Mar. 26, 2015, the entire contents of each of which are hereby incorporated by reference herein in their entireties.

FIELD OF THE INVENTION

The present invention describes a hydrate of 2-isopropoxy-5-methyl-4-(piperidin-4-yl) aniline dihydrochloride, a preparation method of the same, and a use thereof for the preparation of Ceritinib.

BACKGROUND OF THE INVENTION

Lung cancer is a globally highest incident malignancy, and the number of patients is increased by a rate of 3% or more per year due to the environmental and other factors. And 80-85% of the diagnosed patients are attacked by non-small cell lung cancer (NSCLC), wherein, 2%-7% of the patients were induced by the rearrangement of the ALK gene, leading to the accelerated growth of cancer cells and deteriorated conditions. Ceritinib is an oral, selective anaplastic lymphoma kinase (ALK) inhibitor, and in clinical studies, breakthrough progress has been obtained in the treatment of metastatic non-small cell lung cancer (NSCLC) with it. On Apr. 29, 2014, the Food and Drug Administration [FDA] in USA approved the use of Ceritinib for the patients with deteriorated condition after the treatment of Xalkori (crizotinib) or the patients with Xalkori intoleranced and the anaplastic lymphoma kinase positive (ALK+) metastatic non-small cell lung cancer (NSCLC).

The current disclosed literature [J. Med. Chem. 2013, 56, 5675-5690] discloses a preparation method of Ceritinib (LDK378) as follows:

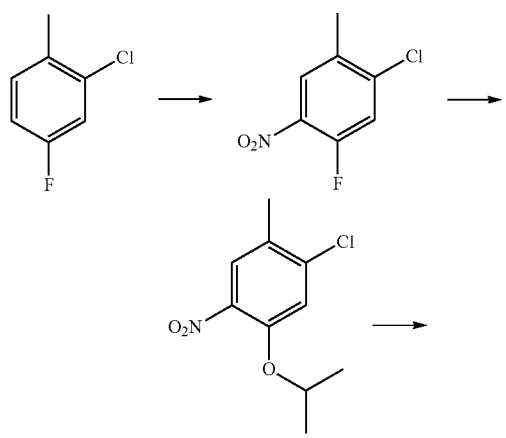

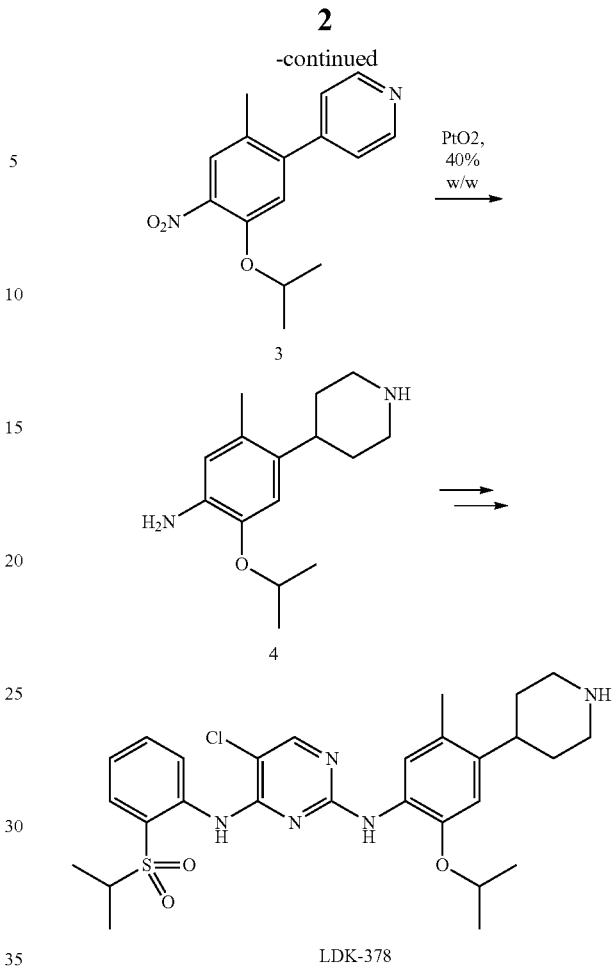

The synthesis of the key intermediate 4 (2-isopropoxy-5-methyl-4-(piperidin-4-yl) aniline) is a very important synthesis step. According to the literature and the current research results, it has been found that impurities in intermediate 4 will be introduced in the final bulk drug, resulting in that the impurity content is difficult to be limited within 0.1% or less. The quality of intermediate 4 is therefore critical to the quality of the final bulk drug. Thus, purification of intermediate 4 is essential, however, the free base form of intermediate 4 is an oily product which cannot be purified by recrystallization, and column chromatography does not meet the requirements of mass production. It is therefore important to find a form by which intermediate 4 can be purified by recrystallization.

SUMMARY OF THE INVENTION

The present invention describes a hydrate form of 2-isopropoxy-5-methyl-4-(piperidin-4-yl) aniline dihydrochloride as an intermediate of Ceritinib. The present invention further provides a preparation method of a substantially pure hydrate of 2-isopropoxy-5-methyl-4-(piperidin-4-yl) aniline dihydrochloride. The substantially pure hydrate of 2-isopropoxy-5-methyl-4-(piperidin-4-yl) aniline dihydrochloride means a hydrate of 2-isopropoxy-5-methyl-4-(piperidin-4-yl) aniline dihydrochloride that has a purity of 95% or more, or even 98% or more, more preferably 99% or more, and a single impurities of 0.2% by weight or less, more preferably 0.1% by weight or less, wherein 2-isopropoxy-5-methyl-4-(piperidin-4-yl) aniline dihydrochloride is intermediate 4 whose structural formula is as follows:

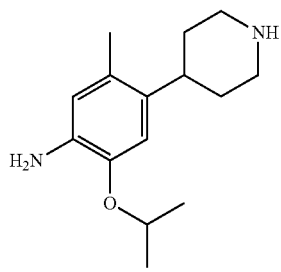

The present inventors have screened a large amount of salts of 2-isopropoxy-5-methyl-4-(piperidin-4-yl) aniline and corresponding crystal forms thereof, and found that 2-isopropoxy-5-methyl-4-(piperidin-4-yl) aniline hydrochloride, in particular the hydrate form of 2-isopropoxy-5-methyl-4-(piperidin-4-yl) aniline dihydrochloride, has a good crystalline form, and is very suitable for recrystallization purification, further, impurity removal effect is also very good and any single impurity can reach 0.1%.

2-isopropoxy-5-methyl-4-(piperidin-4-yl) aniline free base can be prepared by catalytic hydrogenation using the platinum dioxide as reported in the above literature [J. Med. Chem. 2013, 56, 5675-5690], or, the catalytic hydrogenation using palladium on carbon, and then the corresponding hydrochloride may be produced, otherwise, the hydrochloric acid may be added in the process of catalytic hydrogenation, and the hydrogenation is carried out in a corrosion-resistant reactor, resulting in salt directly. Either the water in the heterogeneous catalyst in the catalytic hydrogenation process, or the water added in the salification process, can result in the generation of the corresponding dihydrochloride hydrate.

The solvent of catalytic hydrogenation is preferably selected from C1-C6 primary alcohols, secondary alcohols and tertiary alcohol solvents, which include, for example, methanol, ethanol, propanol, isopropanol, butanol, isobutanol, t-butanol, pentanol, isopentanol and the like, or a combination solvent of an alcoholic solvent and water. The pressure of the catalytic hydrogenation is in a range from 0.5 to 5 MPa, preferably from 1 to 2 MPa, and the reaction temperature thereof is from room temperature to 280° C.

Ceritinib can be prepared by reacting 2-isopropoxy-5-methyl-4-(piperidin-4-yl) aniline free base with a pyrimidine intermediate (WO2008073687), then the Ceritinib bulk drug is obtained (As shown in the following scheme). Pure 2-isopropoxy-5-methyl-4-(piperidin-4-yl) aniline free base can be prepared by neutralizing the purified 2-isopropoxy-5-methyl-4-(piperidin-4-yl) aniline dihydrochloride hydrate with a base to dissociate the salt, then 2-isopropoxy-5-methyl-4-(piperidin-4-yl) aniline free base is formed.

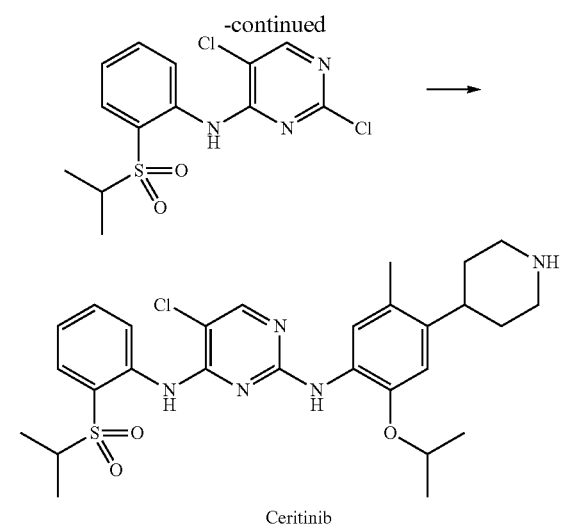

Ceritinib

Alternatively, 2-isopropoxy-5-methyl-4-(piperidin-4-yl) aniline dihydrochloride hydrate is directlly reacted with a pyrimidine intermediate (WO2008073687) to produce the corresponding Ceritinib hydrochloride, the Ceritinib free base is obtained after dissociation. The scheme is as follows:

Ceritinib HCl

DETAILS OF THE INVENTION

The present invention provides a compound having one mole of water, i.e., 2-isopropoxy-5-methyl-4-(piperidin-4-yl) aniline dihydrochloride monohydrate, the structure formula thereof is as follows:

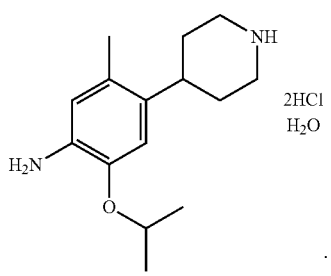 [SMILES: Cc1cc(N)c(OC(C)C)cc1C1CCNCC1]

The present invention further provides a preparation method of 2-isopropoxy-5-methyl-4-(piperidin-4-yl) aniline dihydrochloride monohydrate, comprising the following steps:

(1) dissolving 4-(5-isopropoxy-2-methyl-4-nitro-phenyl) pyridine in an alcoholic solvent, and reducing by hydrogenating reduction via a noble metal catalyst to obtain 2-isopropoxy-5-methyl-4-(piperidin-4-yl) aniline free base;

(2) reacting the 2-isopropoxy-5-methyl-4-(piperidin-4-yl) aniline free base with an alcoholic solution of hydrochloric acid or hydrogen chloride.

Preferably,

The noble metal catalyst in step (1) is one or more selected from platinum oxide, palladium on carbon, and rhodium on carbon.

The molar ratio of the 2-isopropoxy-5-methyl-4-(piperidin-4-yl) aniline free base to the hydrogen chloride in the hydrochloric acid or alcoholic solution of hydrogen chloride in step (2) is 1:2-1:10.

The concentration of the alcoholic solution of hydrochloric acid or hydrogen chloride is from 1% to 40%.

The alcohols described in step (1) and step (2) are independently one or more selected from the group consisting of methanol, ethanol, propanol, isopropanol, butanol, isobutanol, pentanol, 2-pentanol and hexanol.

For the 2-isopropoxy-5-methyl-4-(piperidin-4-yl) aniline dihydrochloride hydrate, it was shown in thermogravimetric analysis (TGA) that the dehydration temperature of the hydrate is higher than 130° C., and weight loss by drying at 120° C. is not more than 1%; The decomposition point of the compound is higher than 230° C. and the weight loss at 170° C. is not more than 7%. Thus the hydrate contains one mole of water, which is lost at a temperature between about 120 to 180° C.

This "hydrate form" is unique in terms of thermodynamic stability, physical parameters, X-ray structure and preparation methods. It should be noted that different samples in the form of specific hydrates may share the same main peak of X-ray powder diffraction (XRPD), but the secondary peaks in the powder pattern may vary. In addition, the term "about" generally means that the difference between the given value and the maximum XRPD value(expressed in degree) is 0.3° or less, more preferably 0.2° or less, and most preferably 0.1° or less. Or, the term "about" means that it falls within the accepted standard of error of the mean value for those skilled in the art. In addition, 2-isopropoxy-5-methyl-4-(piperidin-4-yl) aniline dihydrochloride monohydrate may also have different crystal forms and thus different X-powder diffraction patterns may be shown, but all of them belong to the hydrate concept of the present invention.

For 2-isopropoxy-5-methyl-4-(piperidin-4-yl) aniline dihydrochloride monohydrate of the present invention, the XRPD of one crystal form A thereof exhibits the diffraction peaks where maximum values are at 10.4°, 13.4°, 15.9°, 17.3°, 19.3°, 20.3°, 20.9°, 21.4°, 21.9°, 23.6°, 24.5°, 25.3°, 25.8°, 26.2°, 27.0°, 27.8°, 28.2°, 29.5°, 30.9°, 31.5°, 32.2°, 33.6°, 34.2°, 35.0°±0.2° (2θ degrees), preferably, it has an XRPD pattern as shown in FIG. 1.

The crystal form A of 2-isopropoxy-5-methyl-4-(piperidin-4-yl) aniline dihydrochloride monohydrate shows the following DSC data: dehydrated and melted at 150° C. to 180° C., as determined by differential scanning calorimetry at a scanning rate of 10° C./min (FIG. 2). The decomposition point of the hydrate is higher than 130° C. and the weight loss by drying at 120° C. is not more than 1%. The decomposition point of the compound is higher than 230° C. and the weight loss at 170° C. is not more than 7%, as determined by thermogravimetric analysis and summarized in FIG. 3.

Fourier transform infrared (FT-IR) of the crystal form A of 2-isopropoxy-5-methyl-4-(piperidin-4-yl) aniline dihydrochloride monohydrate shows the main band at the following wave number: 3342.7, 2991.1, 2743.2, 2692.6, 2539.0, 1622.3, 1497.6, 1210.8, 1106.5, 691.8 (wave number, $cm^{-1}$).

The crystal form A of 2-isopropoxy-5-methyl-4-(piperidin-4-yl) aniline dihydrochloride monohydrate can be obtained by using the aforementioned preparation method of the 2-isopropoxy-5-methyl 4-(piperidin-4-yl) aniline dihydrochloride monohydrate.

In an illustrative embodiment, the present invention provides a preparation method of a substantially pure 2-isopropoxy-5-methyl-4-(piperidin-4-yl) aniline dihydrochloride monohydrate, it can also be prepared by means of a mixed solvent which comprises a good solvent, in which the compound is easily soluble, and a poor solvent, in which the compound is hardly soluble, provided that the crystallization may be conducted from the mixture by agitating the solvent mixture. Examples of the good solvent include one or more selected from the group consisting of water and methanol. Examples of the poor solvent include one or more selected from the group consisting of ethanol, isopropanol, ethyl acetate, tetrahydrofuran and acetone.

Specifically, the present invention provides a preparation method of a substantially pure 2-isopropoxy-5-methyl-4-(piperidin-4-yl) aniline dihydrochloride monohydrate, comprising the following steps:

(1) mixing a good solvent with a poor solvent to prepare a mixed solvent;

(2) mixing the 2-isopropoxy-5-methyl-4-(piperidin-4-yl) aniline dihydrochloride monohydrate with the mixed solvent, then stirring and heating to reflux and dissolve to give a clear solution(the heating temperature is preferably 50° C. to 110° C.);

(3) cooling to −10° C. to 30° C., crystallizing, filtering, gathering the filter cake, and drying to give a substantially pure 2-isopropoxy-5-methyl-4-(piperidin-4-yl) aniline dihydrochloride monohydrate. The term "substantially pure" means that the purity is 95% or more, or even 98% or more, and more preferably 99% or more.

Wherein,

The good solvent in step (1) is one or more selected from the group consisting of water and methanol; the poor solvent is one or more selected from the group consisting of ethanol, isopropanol, ethyl acetate, tetrahydrofuran and acetone; preferably, the good solvent is water, and the poor solvent is isopropanol;

The volume ratio of the good solvent to the poor solvent in step (1) is 1:1 to 1:100.

The mass-to-volume ratio (g/ml) of 2-isopropoxy-5-methyl-4-(piperidin-4-yl) aniline dihydrochloride monohydrate to the mixed solvent in step (2) is 1:1 to 1:100.

In an illustrative embodiment, the 2-isopropoxy-5-methyl-4-(piperidin-4-yl) aniline provided by the present application may be prepared from 4-(5-isopropoxy-2-methyl-4-nitro-phenyl) pyridinium bromide salts, and it may also be prepared by catalytic hydrogenating 4-(5-isopropoxy-2-methyl-4-nitro-phenyl) pyridine in C1-C6 alcohol (e.g., methanol, ethanol, isopropanol, etc.) with platinum oxide or palladium.

The present invention further provides a use of the 2-isopropoxy-5-methyl-4-(piperidin-4-yl) aniline dihydrochloride monohydrate and the crystal form A thereof in the preparation of Ceritinib.

BRIEF DESCRIPTIONS OF THE DRAWINGS

DESCRIPTION OF THE EMBODIMENTS

Figures 1, 2:
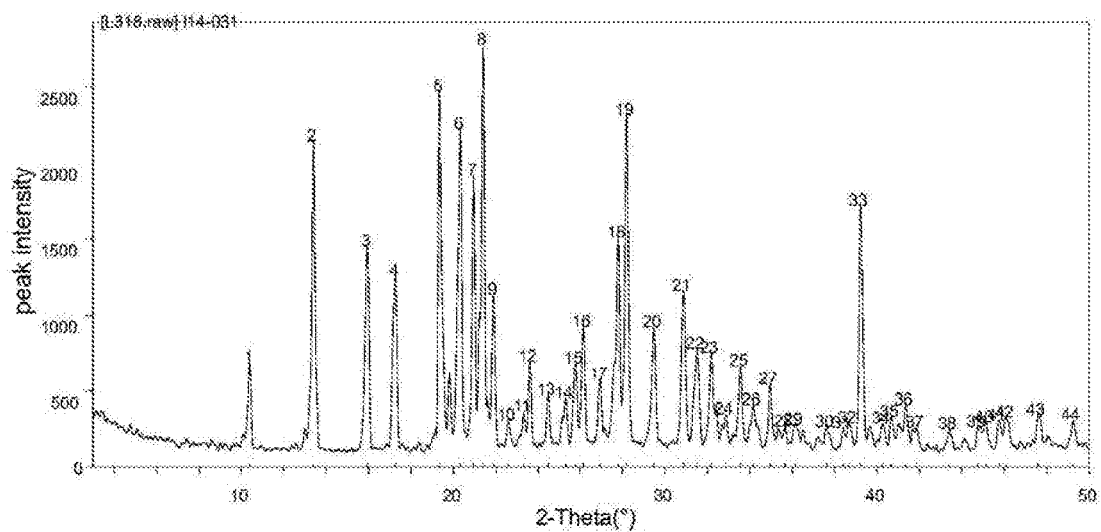
FIG. 1 is an X-ray powder diffraction pattern of crystal form A of 2-isopropoxy-5-methyl-4-(piperidin-4-yl) aniline dihydrochloride monohydrate.
FIG. 2 is a differential scanning calorimetry curve of crystal form A of 2-isopropoxy-5-methyl-4-(piperidin-4-yl) aniline dihydrochloride monohydrate.
Figure 3:
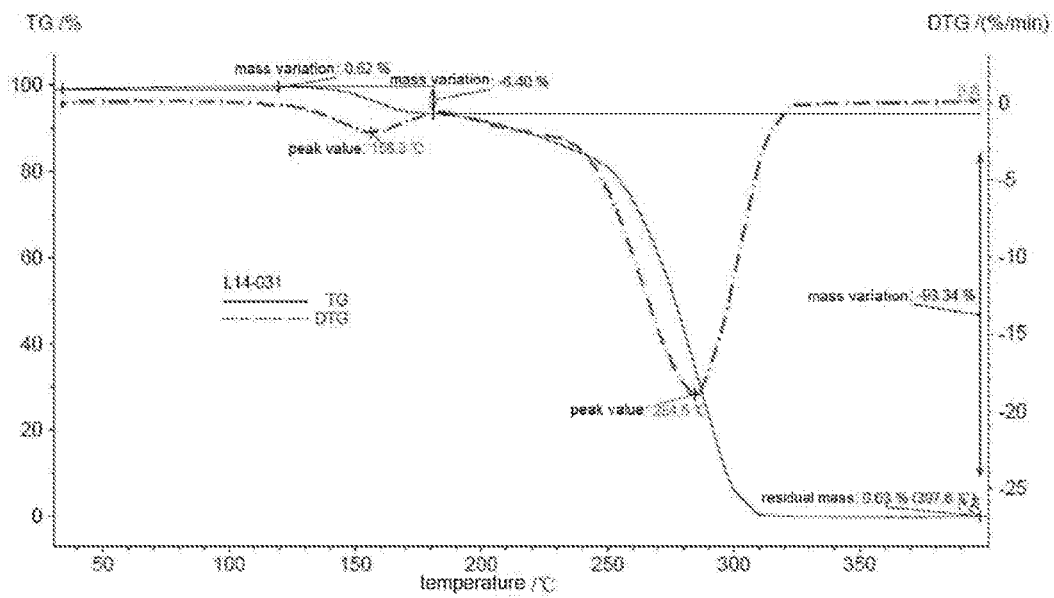
FIG. 3 is differential scanning calorimetry curve and thermogravimetric curve of crystal form A of 2-isopropoxy-5-methyl-4-(piperidin-4-yl) aniline dihydrochloride monohydrate.
Figure 4:
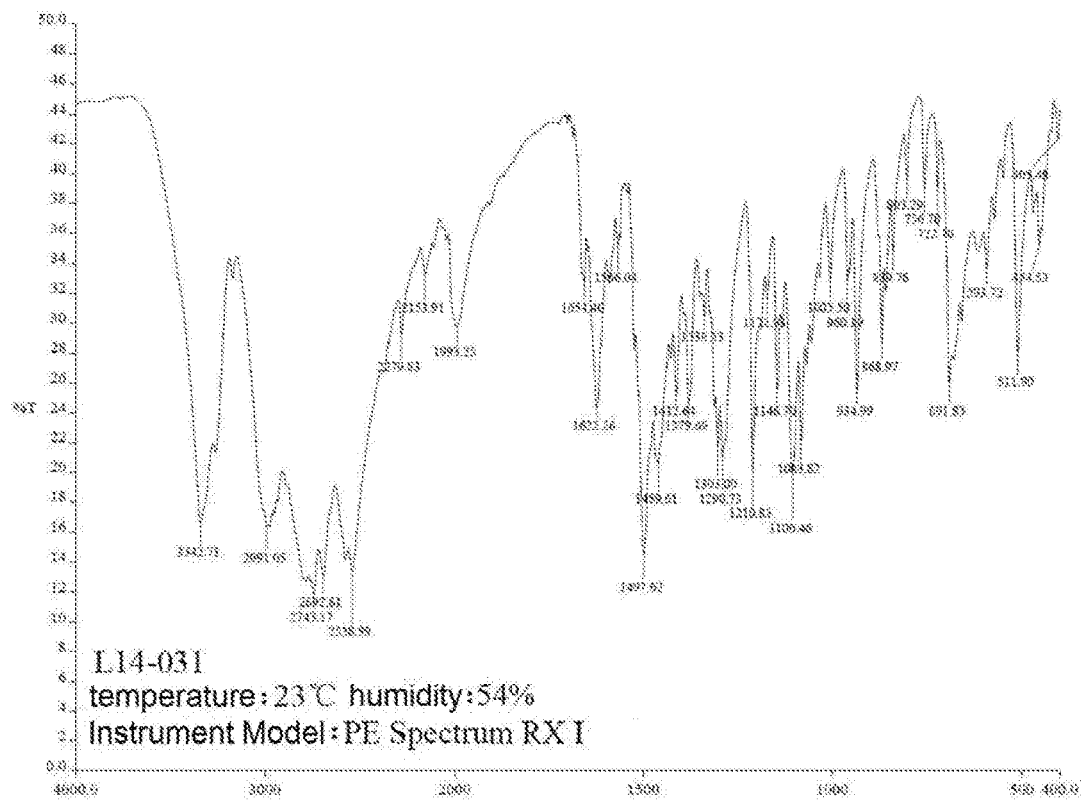
FIG. 4 is an infrared spectrum of crystal form A of 2-isopropoxy-5-methyl-4-(piperidin-4-yl) aniline dihydrochloride monohydrate.

The present invention may be fully understood by the following examples, but they are not intended to limit the invention in any way.

Example 1

Preparation of 2-chloro-4-fluoro-5-nitrotoluene

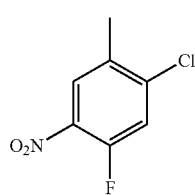

135 ml of concentrated sulfuric acid was added into the reaction flask, and cooled in an ice bath under stirring, 43.4g fuming nitric acid was then added therein dropwise. After the completion of addition, the mixture was stirred continuously for 30 min to form a mixed acid. Meanwhile, 315 ml of concentrated sulfuric acid and 90.0 g of 2-chloro-4-fluorotoluene were added in another three-necked flask. The abovementioned mixed acid of nitric acid and sulfuric acid was added to the sulfuric acid solution of 2-chloro-4-fluorotoluene under cooling in an ice-salt bath, and the reaction was continued for 1 to 2 hours. The reaction solution was slowly added to the crushed ice under stirring to quench, and then extracted with ethyl acetate twice. The ethyl acetate layers was combined, and washed twice with water and once with saturated brine. The organic phase was concentrated to dryness to give oily 2-chloro-4-fluoro-5-nitrotoluene.

H NMR Data
$^1$H NMR(CDCl$_3$, 400 MHz): δ 7.95(d, 3.8, 1H), 7.51(d, 4.2, 1H), 2.45(s, 3H).

Example 2

Preparation of 2-chloro-4-isopropyoxy-5-nitrotoluene

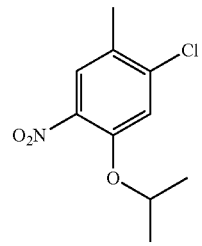

2-chloro-4-fluoro-5-nitrotoluene was dissolved in 1200 ml of isopropanol and the solution was added in a 2 L of a three-necked flask. 429 g of anhydrous potassium carbonate powder was added therein. The mixture was heated to reflux under stirring. The reaction was conducted for about 40 hours under reflux. Most of the isopropanol was removed via concentration. 2 L of water was added and the mixture was extracted with ethyl acetate twice. The ethyl acetate layer was combined and washed with water. Ethyl acetate layer was concentrated to give 2-chloro-4-isopropoxy-5-nitrotoluene as a brown substance.

H NMR Data
$^1$H NMR (CDCl$_3$): δ 7.71(s, 1H), 7.07(s, 1H), 4.61(m, 1H), 2.34(s, 3H), 1.40(d, 3.2, 6H).

Example 3

Preparation of 4-(5-isopropoxy-2-methyl-4-nitro-phenyl)pyridine

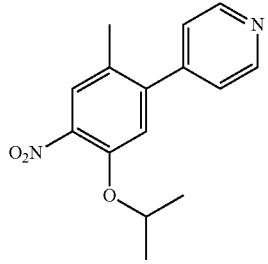 [SMILES: Cc1cc([N+](=O)[O-])c(OC(C)C)cc1-c1ccncc1]

78 g of 2-chloro-4-isopropoxy-5-nitrotoluene, 42 g of 4-pyridineboric acid, 97 g of potassium carbonate, 780 mL of dioxane, 390 mL of purified water, 7.67 g of palladium acetate, and 35.85 g of triphenylphosphine were added into a 2 L three-necked flask. Under the protection of nitrogen, the reaction was conducted for 24 hours under stirring and refluxing. Most of the dioxane was removed via concentration. 1.5 L of water was added and the mixture was extracted with ethyl acetate twice. The ethyl acetate layers were combined and washed with saturated brine twice, and the organic phase was concentrated to dryness to give a 4-(5-isopropoxy-2-methyl-4-nitro-phenyl) pyridine as a brown solid, i.e. the compound 3.

H NMR Data $^1$H NMR(CDCl$_3$): δ 8.72(m, 2H), 7.71(s, 1H), 7.31(m, 2H), 6.89(s, 1H), 4.63(m, 1H), 2.21(s, 3H), 1.38(d, 3.0, 6H).

Example 4

Preparation of 4-(5-isopropoxy-2-methyl-4-nitro-phenyl)-1-benzyl-pyridinium bromide

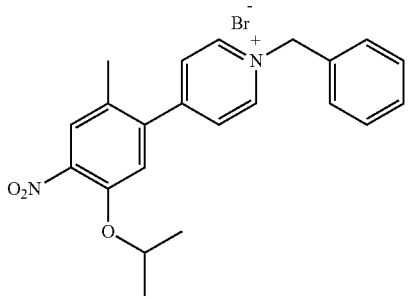

(4)

4-(5-isopropoxy-2-methyl-4-nitro-phenyl) pyridine (33 g), bromobenzyl (31.08 g) and tetrahydrofuran (330 mL) were added to a 1000 mL reaction flask. The mixture was stirred and reacted by heating to reflux overnight. After the resultant was cooled to room temperature, 330 mL of heptane was slowly added therein. The resultant was stirred continuously for 1 hour and then filtered. The filter cake was dried to give 4-(5-isopropyl-2-methyl-4-nitro-phenyl)-1-benzyl-pyridinium bromide. Purity is 99%.

MS(ESI+): 363.2(M)$^+$. $^1$H NMR(DMSO-d$_6$): δ 9.40(d, 3.4, 2H), 8.33(d, 3.4, 2H), 7.89(s, 1H), 7.65-7.68(m, 2H), 7.45-7.51(m, 3H), 7.43(s, 1H), 5.96(s, 2H), 4.84-4.88(m, 1H), 2.25(s, 3H), 1.27(d, 3.0, 6H).

Example 5

Preparation of 2-isopropoxy-5-methyl-4-(1-benzyl-1,2,3,6-tetrahydropyridin-4-yl)-phenylamine

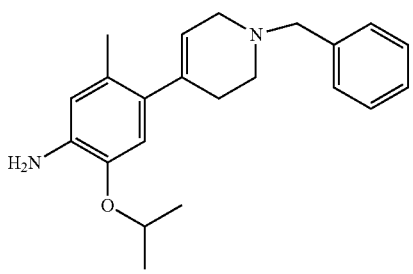

(3)

4-(5-isopropoxy-2-methyl-4-nitro-phenyl)-1-benzyl-pyridinium bromide (17.8 g) and methanol (535 mL) were added to a 1000 mL reaction flask. The mixture was stirred and cooled. NaBH$_4$ (15.13 g) was added in portions. 9 mL of 3N hydrochloric acid was slowly added therein. It is confirmed that no NaBH$_4$ remained. Then the solvent is removed by evaporating, and then 190 mL of water was added and the mixture was stirred. After that, ethyl acetate (190 mL) was added therein, the liquid was separated, the organic phase was collected, and the aqueous phase was further extracted with ethyl acetate (190 mL×2). The organic phases were then combined, washed once with water and saturated brine (190 mL) respectively. The organic phase was evaporated to dryness to give 2-isopropoxy-5-methyl-4-(1-benzyl-1,2,3,6-tetrahydropyridin-4-yl)-phenylamine.

MS(ESI+):337.3(M+1)$^+$. $^1$H NMR(CDCl$_3$): δ 7.26-7.44 (m, 5H), 6.59(s, 1H), 6.53(s, 1H), 5.50(m, 1H), 4.44(m, 1H), 3.72(s, 2H), 3.19-3.24(m, 2H), 2.72-2.80(m, 2H), 2.41-2.44 (m, 2H), 2.16(m, 3H), 1.33(d, 3.0, 6H).

Example 6

Preparation of 2-isopropoxy-5-methyl-4-(1-benzyl-1,2,3,6-tetrahydropyridin-4-yl)-phenylamine hydrochloride

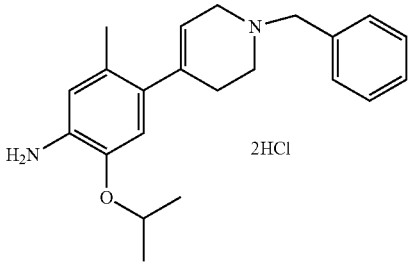 [SMILES: Cc1cc(N)c(OC(C)C)cc1C1=CCN(Cc2ccccc2)CC1]

2-isopropoxy-5-methyl-4-(1-benzyl-1,2,3,6-tetrahydropyridin-4-yl)-phenylamine (12.5 g) was dissolved in 125 mL of isopropanol, the mixture was cooled, and the solution of hydrogen chloride in isopropanol was added therein dropwisely until pH=1. The resultant was filtered and the filter cake was collected and dried in vacuum to give 2-isopropoxy-5-methyl-4-(1-benzyl-1,2,3,6-tetrahydropyridin-4-yl)-phenylamine hydrochloride. Purity is 99%.

MS(ES+): 337.3(M+1)$^+$. $^1$H NMR(DMSO-d$_6$): δ 7.71-7.74(m, 2H), 7.45-7.47(m, 3H), 7.22(s, 1H), 6.90(s, 1H), 5.56(s, 2H), 4.65-4.68(m, 1H), 4.36-4.46(m, 2H), 3.60-3.72 (m, 2H), 3.51-3.54(m, 1H), 3.20-3.22(m, 1H), 2.85-2.89(m, 1H), 2.20(s, 1H), 1.28(d, 2.8 6H).

Example 7

2-isopropoxy-5-methyl-4-(piperidin-4-yl) aniline dihydrochloride monohydrate

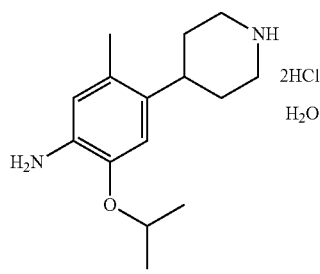

2-isopropoxy-5-methyl-4-(1-benzyl-1,2,3,6-tetrahydropyridin-4-yl)-phenylamine hydrochloride (10.05 g), methanol (100 mL) and 0.5 g of palladium on carbon were added to the hydrogenation vessel. The vessel was purged with nitrogen. It was heated to 90° C. and pressurized to 1.0 MPa, and the reaction was conducted for 8 hours. The resultant was cooled to room temperature, and then filtered to remove the catalyst. The filtrate was evaporated to remove the solvent and 100 mL of IPA was added thereto. HCl/IPA was added dropwise under cooling in an ice bath to adjust the pH to acidity. After filtration, the filter cake was washed with IPA (10 mL). Then it was dried to obtain 2-isopropoxy-5-methyl-4-(piperidin-4-yl) aniline dihydrochloride monohydrate. Purity is 99%.

MS(ES+): 249.3(M+1)$^+$. $^1$H NMR(DMSO-d): δ 7.18(s, 1H), 6.92(s, 1H), 4.62-4.65(m, 1H), 3.29(d, 4.8, 2H), 2.97-3.03(m, 3H), 2.22(s, 1H), 1.97-2.00(m, 2H), 1.76(d, 5.2, 2H), 1.29(d, 2.4, 6H).

Example 8

2-isopropoxy-5-methyl-4-(piperidin-4-yl) aniline dihydrochloride monohydrate

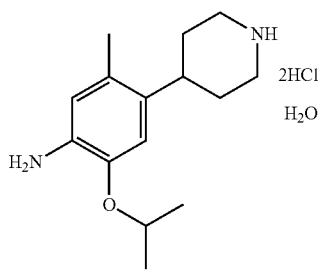

4-(5-isopropoxy-2-methyl-4-nitro-phenyl) pyridine (1 Kg) obtained in Example 3, methanol (10 L) and 100 g of 10% palladium on carbon were added into a hydrogenation vessel. The vessel was purged with nitrogen. It was heated to 100° C. and pressurized to 1 to 1.5 MPa, and the reaction was conducted for 8 hours and then completed. The resultant was cooled to room temperature, and then filtered to remove the catalyst. The solvent was distilled off from the filtrate, and 5 L of isopropanol was added to give 2-isopropoxy-5-methyl-4-(piperidin-4-yl) aniline free base. The isopropanol solution of hydrogen chloride was added dropwise under cooling in an ice bath to adjust the pH to acidity. After filtration, the filter cake was washed with isopropanol (1 L). Then it was dried to obtain 2-isopropoxy-5-methyl-4-(piperidin-4-yl) aniline dihydrochloride monohydrate. Purity is 99%. MS(ES+): 249.3(M+1)$^+$. $^1$H NMR(DMSO-d$_6$): δ 7.18 (s, 1H), 6.92(s, 1H), 4.62-4.65(m, 1H), 3.29(d, 4.8, 2H), 2.97-3.03(m, 3H), 2.22(s, 1H), 1.97-2.00(m, 2H), 1.76(d, 5.2, 2H), 1.29(d, 2.4, 6H).

Example 9

2-isopropoxy-5-methyl-4-(piperidin-4-yl) aniline dihydrochloride monohydrate

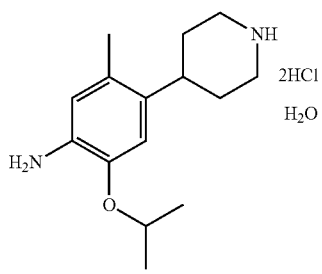

4-(5-isopropoxy-2-methyl-4-nitro-phenyl) pyridine (1 Kg) obtained in Example 3, isopropanol (10 L) and 100 g of 5% palladium on carbon were added into a hydrogenation vessel. The vessel was purged with nitrogen. It was heated to 110° C. and pressurized to 1 to 1.5 MPa, and the reaction was conducted for 8 hours and then completed. The resultant was cooled to room temperature, and then filtered to remove the catalyst. The solvent was distilled off from the filtrate, and then 5 L of isopropanol was added to give 2-isopropoxy-5-methyl-4-(piperidin-4-yl) aniline free base. The isopropanol solution of hydrogen chloride was added dropwise under cooling in an ice bath to adjust the pH to acidity. After filtration, the filter cake was washed with isopropanol (1 L). Then it was dried to obtain 2-isopropoxy-5-methyl-4-(piperidin-4-yl) aniline dihydrochloride monohydrate. Purity is 99%. MS(ES+): 249.3(M+1)$^+$. $^1$H NMR(DMSO-d$_6$): δ 7.18 (s, 1H), 6.92(s, 1H), 4.62-4.65(m, 1H), 3.29(d, 4.8, 2H), 2.97-3.03(m, 3H), 2.22(s, 1H), 1.97-2.00(m, 2H), 1.76(d, 5.2, 2H), 1.29(d, 2.4, 6H).

Example 10

Purification of 2-isopropoxy-5-methyl-4-(piperidin-4-yl) aniline dihydrochloride monohydrate

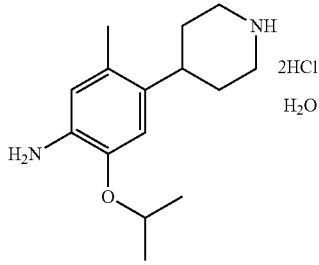

2-isopropoxy-5-methyl-4-(piperidin-4-yl) aniline dihydrochloride monohydrate (10.0 g), isopropanol (100 mL) and water (6.0 g) were added in the reaction flask. The vessel was purged with nitrogen. The mixture was stirred and heated to reflux and dissolved clarification. The resultant was cooled to 0° C. and crystallized. After filtration, the filter cake was collected. Then it was dried to obtain 2-isopropoxy-5-methyl-4-(piperidin-4-yl) aniline dihydrochloride monohydrate. Purity is 99.5%. MS(ES+): 249.3(M+1)$^+$. 1H NMR(DMSO-d$_6$): δ 7.18(s, 1H), 6.92(s, 1H), 4.62-4.65 (m, 1H), 3.29(d, 4.8, 2H), 2.97-3.03(m, 3H), 2.22(s, 1H), 1.97-2.00(m, 2H), 1.76(d, 5.2, 2H), 1.29(d, 2.4, 6H).

Example 11

Preparation of 5-chloro-N-(2-isopropoxy-5-methyl-4-(piperidin-4-ylphenyl)-N-2-(isopropylsulfonyl) phenyl)-2,4-diamine dihydrochloride

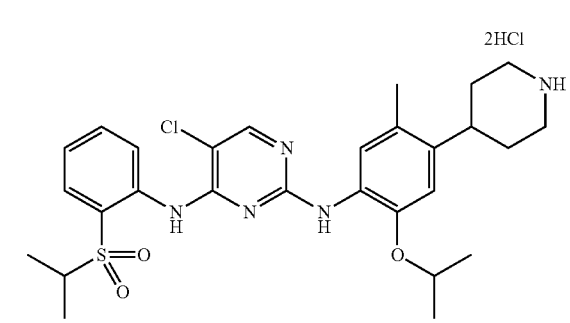 [SMILES: Cc1cc(Nc2ncc(Cl)c(Nc3ccccc3S(=O)(=O)C(C)C)n2)c(OC(C)C)cc1C1CCNCC1]

2-isopropoxy-5-methyl-4-(piperidin-4-yl) aniline dihydrochloride monohydrate (17.00 g) and 2,5-dichloro-N-(2-(isopropylsulfonyl)phenyl) pyrimidin-4-amine (commercially available) (18.32 g) were added to a 500 mL three-necked flask, and 170 mL of isopropanol was added thereto. The mixture was stirred, heated to reflux and reacted overnight. After cooling to room temperature, the mixture was filtered and washed, the filter cake was collected. The filter cake was dried to obtain 5-chloro-N-(2-isopropoxy-5-methyl-4-(piperidin-4-ylphenyl)-N-2-(isopropylsulfonyl) phenyl)-2,4-diamine dihydrochloride. Purity is 99%.

MS(ESI+): 558.1(M+1)$^+$. $^1$H NMR(DMSO-d$_6$): δ 10.15 (s, 1H), 9.18-9.38(m, 3H), 8.54(s, 1H), 8.06-8.08(m, 1H), 7.92-7.94(d, 3.2, 1H)7.73-7.77(t, 3.8, 1H), 7.54-7.58(t, 4.0, 1H), 7.31(s, 1H), 6.82(s, 1H), 4.51-4.57(m, 1H), 3.45-3.52 (m, 1H), 3.30-3.32(d, 5.8, 2H), 2.93-3.03(m, 3H), 1.89-1.99 (m, 5H), 1.73-1.77(d, 6.4, 2H), 1.24-1.26(d, 3.2, 6H), 1.10-1.111(d, 3.2, 6H).

Example 12

Preparation of 5-chloro-N-(2-isopropoxy-5-methyl-4-(piperidin-4-ylphenyl)-N-2-(isopropylsulfonyl) phenyl)-2,4-diamine (LDK-378)

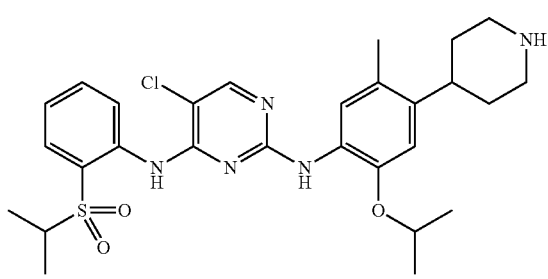 [SMILES: Cc1cc(Nc2ncc(Cl)c(Nc3ccccc3S(=O)(=O)C(C)C)n2)c(OC(C)C)cc1C1CCNCC1]

5-chloro-N-(2-isopropoxy-5-methyl-4-(piperidin-4-yl-phenyl)-N-2-(isopropylsulfonyl) phenyl)-2,4-diamine dihydrochloride (6.31 g) was added to a 50 mL three-necked flask. 19 g of acetone aqueous solution (3: 1, v/v) was added. The mixture was stirred and heated to 55° C., and 10 g of about 10% aqueous NaOH was added dropwise. After the dripping was complete, the mixture was cooled to room temperature, diluted with 42 g of purified water, and continuously stirred for 1 hour. After filtration, the filter cake was collected and dried in vacuum to give 5-chloro-N-(2-isopropoxy-5-methyl-4-(piperidin-4-ylphenyl)-N-2-(isopropylsulfonyl)phenyl)-2,4-diamine. Purity is not less than 99%, and a single impurity is not higher than 0.1%.

MS(ESI+):558.1(M+1)$^+$. $^1$H NMR(DMSO-d$_6$):δ 8.44(d, 3.4, 1H), 8.20(s, 1H), 8.02(s, 1H), 7.80-7.82(m, 1H), 7.56-7.60(m, 1H), 7.49(s, 1H), 7.30-7.33(m, 1H), 6.80(s, 1H), 4.49-4.54(m, 1H), 3.42-3.47(m, 1H), 3.02(d, 4.8, 2H), 2.57-2.72(m, 3H), 2.10(m, 3H), 1.47-1.60(m, 4H), 1.21(d, 2.4, 6H), 1.14(d, 2.6, 6H).

The invention claimed is:

1. A crystal form A of 2-isopropoxy-5-methyl-4-(piperidin-4-yl)aniline dihydrochloride monohydrate, wherein the X-ray powder diffraction pattern thereof exhibits characteristic peaks at the following 2θ±0.2 degrees: 10.4°, 13.4°, 15.9°, 17.3°, 19.3°, 20.3°, 20.9°, 21.4°, 21.9°, 23.6°, 24.5°, 25.3°, 25.8°, 26.2°, 27.0°, 27.8°, 28.2°, 29.5°, 30.9°, 31.5°, 32.2°, 33.6°, 34.2°, 35.0°.

2. A method of preparing the crystal form A of 2-isopropoxy-5-methyl-4-(piperidin-4-yl) aniline dihydrochloride monohydrate according to claim 1, the method comprising:
   dissolving 4-(5-isopropoxy-2-methyl-4-nitro-phenyl) pyridine in an alcoholic solvent, and reducing by hydrogenating reduction via a noble metal catalyst to obtain 2-isopropoxy- 5-methyl-4-(piperidin-4-yl) aniline free base; and
   reacting the 2-isopropoxy-5-methyl-4-(piperidin-4-yl) aniline free base with an alcoholic solution of hydrochloric acid or hydrogen chloride.

3. The crystal form A of 2-isopropoxy-5-methyl-4-(piperidin-4-yl)aniline dihydrochloride monohydrate according to claim 1, wherein the crystal form A of 2-isopropoxy-5-methyl-4-(piperidin-4-yl)aniline dihydrochloride monohydrate exhibits a decomposition point at about 230° C. as determined by differential scanning calorimetry.

* * * * *